(12) United States Patent
Sorin

(10) Patent No.: US 6,514,770 B1
(45) Date of Patent: Feb. 4, 2003

(54) IMMUNOASSAY

(75) Inventor: Takaaki Sorin, Yokohama (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/628,559

(22) Filed: Jul. 28, 2000

(30) Foreign Application Priority Data

Jul. 30, 1999 (JP) .............................. 11-216318

(51) Int. Cl.⁷ ............................... G01N 33/53
(52) U.S. Cl. .................... 436/518; 436/501; 436/517; 436/536; 436/539; 436/2; 436/8; 435/7.1; 435/7.94
(58) Field of Search ................. 436/501, 517, 436/518, 536, 539, 2, 8; 435/7.1, 7.94

(56) References Cited

U.S. PATENT DOCUMENTS

| | | | | |
|---|---|---|---|---|
| 3,813,168 A | * | 5/1974 | Honkawa | |
| 4,136,959 A | * | 1/1979 | Honkawa et al. | |
| 4,197,088 A | * | 4/1980 | Meserol et al. | |
| 4,225,233 A | * | 9/1980 | Ogan | |
| 4,743,561 A | * | 5/1988 | Shaffar | |
| 4,954,435 A | * | 9/1990 | Krauth | |
| 4,988,630 A | * | 1/1991 | Chen et al. | |
| 5,093,271 A | * | 3/1992 | Yamamoto | |
| 5,464,749 A | * | 11/1995 | Schwarzberg et al. | |

FOREIGN PATENT DOCUMENTS

JP    2-87063    3/1990

OTHER PUBLICATIONS

Nichols et al., Agglutination and Agglutination Inhibition Assays. Manual of Clinical Laboratory Immunology. pp. 49–56. 2$^{nd}$ Ed. 1980.*

* cited by examiner

*Primary Examiner*—Bao-Thuy L. Nguyen
(74) *Attorney, Agent, or Firm*—Wenderoth, Lind & Ponack, L.L.P.

(57) ABSTRACT

Immunoassay methods for measuring the concentration of an analyte in a test specimen are described. The methods use an immunoreagent, where one of the analyte and the immunoreagent is an antigen, and the other of the analyte and the immunoreagent is an antibody which specifically binds to the antigen. An important feature distinguishing these immunoassays over conventional immunoassays is that the standard sample containing a known concentration of analyte is measured in the same reaction vessel as the test specimen containing an unknown amount of analyte.

17 Claims, 10 Drawing Sheets concentration of T3 (μg/mL)

dark

IMMUNOASSAY

BACKGROUND OF THE INVENTION

1. Field of the Invention

The present invention relates to an immunoassay for measuring the concentration of an object of measurement contained in a specimen by means of an immuno-reagent comprising an antigen or antibody.

2. Description of the Related Art

Heretofore, there have been known various immunoassays making use of an antigen-antibody reaction, such as radioimmunoassay (RIA), enzyme immunoassay (EIA), turbidimetric immunoassay (TIA) and latex agglutination immunoassay (LPIA).

In these immunoassays, the concentration of an object of measurement contained in a specimen is determined from its analytical measurement values (absorbance, transmittance, turbidity, fluorescence, reaction rate and other measured physical values). Calibration for plotting the relationship between the concentration and analytical measurement values of an object of measurement contained in a standard sample is carried out by measuring the standard sample containing the object of measurement in a known concentration in advance so as to determine the concentration of the object of measurement through comparison with the calibration curve. All of these conventional immunoassays are premised on that the specimen and the standard sample are measured in different reaction vessels and that these measurements are always carried out under the same conditions.

However, since there are temperature variations (such as temperatures of apparatus, room, reagent, etc.), variations derived by the stability of the reagent, variations caused by the use state of the reagent (for example, changes in reactivity caused by contamination or the like, the evaporation of water from a reagent bottle, decrease of activity, etc.) in fact, when measurement is newly carried out the following day or several days after the end of a set of continuous measurements or when the lot of reagents is changed, a calibration curve must be newly prepared right before the start of measurement in order to maintain measurement accuracy. That is, in these immunoassays, calibration takes time and it is difficult to make effective use of an immuno-reagent. Even when this calibration is carried out, it is difficult to eliminate an error caused by within-day changes (temperature variations, changes in the intensity of light of a light source, fluctuations in a detector, etc.).

Meanwhile, the standard sample is measured at one point or several points right before the start of measurement to correct the previously prepared calibration curve in order to make effective use of an immuno-reagent.

However, even in this immunoassay, to further improve measurement accuracy, a calibration curve is preferably corrected in advance for each specimen, which is disadvantageous from the viewpoints of time and cost.

Then, an immunoassay for measuring the concentration of an object of measurement effectively and accurately without wasting an immuno-reagent and time has been desired.

SUMMARY OF THE INVENTION

To meet this demand, the inventors of the present invention have conducted intensive studies and have found that a reaction between an immuno-reagent and a standard sample containing an object of measurement in a certain concentration (known concentration), and a reaction between the immuno-reagent and a specimen, are carried out in the same reaction vessel continuously to solve the above problem. The present invention has been thus accomplished based on this finding.

That is, a first aspect of the present invention is a method of immunoassay for measuring the concentration of an object of measurement contained in a specimen by means of an immuno-reagent comprising an antigen or antibody for the object of measurement, characterized by comprising: a standard reaction step of reacting a standard sample containing the object of measurement in a certain concentration with the immuno-reagent in a reaction solution; a specimen reaction step of mixing and reacting the reaction solution of the standard reaction step with the specimen; and a step of determining the concentration of the object of measurement contained in the specimen by comparing the reactivity of the standard reaction step with the reactivity of the specimen reaction step.

A second aspect of the present invention is a method of immunoassay for measuring the concentration of an object of measurement contained in a specimen by means of an immuno-reagent comprising an antigen or antibody for the object of measurement, characterized by comprising: a standard reaction step of reacting a standard sample containing the object of measurement in a certain concentration with an immuno-reagent in a reaction solution; a specimen reaction step of mixing and reacting the reaction solution of the standard reaction step with the specimen; a step of correcting the previously prepared calibration curve using the reactivity of the standard reaction step; and a step of determining the concentration of the object of measurement contained in the specimen from the corrected calibration curve and the reactivity of the specimen reaction step.

A third aspect of the present invention is a method of immunoassay for measuring the concentration of an object of measurement contained in a specimen by means of an immuno-reagent comprising an antigen or antibody for the object of measurement, comprising: two or more standard reaction steps of mixing and reacting two or more standard samples with a reaction solution containing the immuno-reagent sequentially; a specimen reaction step of mixing and reacting the reaction solution of the last standard reaction step with the specimen; a step of preparating a calibration curve from the reactivity of each standard reaction step; and a step of determining the concentration of the object of measurement contained in the specimen by using the calibration curve and the reactivity of the specimen reaction step, wherein at least the standard samples of a second or later standard reaction steps contain the object of measurement in a certain concentration.

A fourth aspect of the present invention is an immunoassay test kit and an immunoassay apparatus used for the above method of immunoassay.

DETAILED DESCRIPTION OF THE PREFERRED EMBODIMENTS

Figure 1:
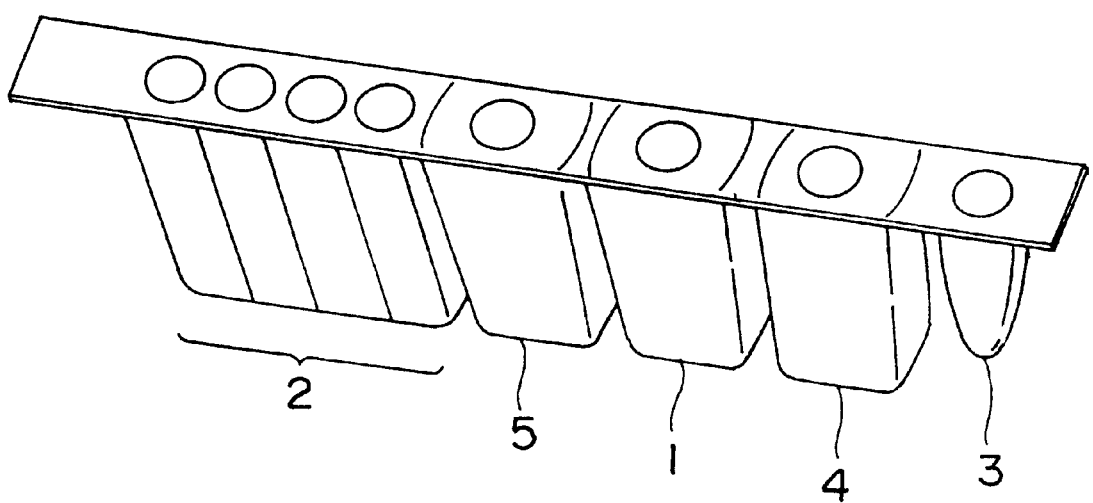
FIG. 1 shows a test kit used in the present invention.

The present invention relates to a method of immunoassay for measuring the concentration of an object of measurement contained in a specimen by means of an immuno-reagent comprising an antigen or antibody for the object of measurement.

The specimen used in the present invention is generally a biosample such as whole blood, serum, plasma, urine, saliva, spinal fluid, fecal matter, or puncture fluid. The object of measurement contained in the specimen is generally an antigen or antibody, for example, plasma protein such as albumin, immunoglobulin or complement; tumor-related antigen such as α-fetoprotein(AFP), CA19-9, carcinoembryonic antigen(CEA) or prostatic acid phosphatase(PAP); infectious desease-related antigen/antibody such as hepatitis B, hepatitis C, syphilis, HIV or CRP; blood coagulation fibrinolysis-related substance such as fibrin/fibrinogen degradation product, D dimer or antithrombin III; myocardial infarction-related protein such as myoglobin or CK-MB; hormone such as thyroid stimulating hormone (TSH), follicle stimulating hormone (FSH), thyroxine (T4), insulin or human chorionic gonadotropin; or drug such as digoxin or theophylline.

The method of immunoassay of the present invention can be used in the following known immunoassays.

<1> an immunoassay making use of antigen-antibody agglutination reaction caused by immunological binding between an antigen or antibody contained in an immuno-reagent and an object of measurement <2> the immunoassay according to the above <1> using dissolved antibody or antigen as an immuno-reagent <3> the immunoassay according to the above <1> using insoluble carrier particles having an antibody or antigen immobilized thereto as an immuno-reagent <4> the immunoassay according to any one of the above <1>–<3> for measuring the agglutination caused by immunoreaction by turbidity obtained by measuring absorbance or scattered light <5> an immunoassay using an immuno-reagent obtained by labeling an antibody or antigen with a fluorescent dye or fluorescent particle as an immuno-reagent <6> the immunoassay according to the above <5> for observing changes in rotation relaxation time caused by changes in the molecular size of a labeled antibody, labeled antigen or immunocomplex thereof due to immunological binding between an antigen or antibody contained in an immuno-reagent and the object of measurement <7> the immunoassay according to the above <6> for observing changes in rotation relaxation time by eliminating fluorescent polarization <8> an immunoassay for observing an energy transfer reaction caused by a reduction in the distance between two different fluorescent dyes due to immunological binding between an antigen or antibody contained in an immuno-reagent and the object of measurement using two immuno-reagents obtained by labeling antibodies or antigens with the different fluorescent dyes <9> the immunoassay according to the above <8> for measuring an energy transfer reaction from an increase or decrease in the amount of light emitted from a fluorescent dye or an increase or decrease in the amount of light emitted from a fluorescent dye at different light emission time <10> an immunoassay for observing immunological binding between an object of measurement and an immuno-reagent on a solid phase using an antigen or antibody immobilized to a solid-phase carrier as an immuno-reagent <11> the immunoassay according to the above <10> for observing immunological binding from surface plasmon resonance <12> the immunoassay according to the above <5> and <10> for observing immunological binding from a fluorescence excited by an evanescent wave <13> the immunoassay according to the above <10> for observing immunological binding from a change in the frequency of a quartz oscillator <14> the immunoassay according to the above <10> for observing immunological binding from a change in potential or current of an electrode <15> the immunoassay according to the above <10> for observing immunological binding from a change in current or resistance caused by a change of a quantity of an ion channel.

The method of immunoassay of the present invention is particularly effectively used in homogeneous immunoassay.

In the present invention, the following are used as "reactivity" to be compared.

A. the reaction rate of particle agglutination caused by an antigen-antibody reaction. This can be calculated from an average absorbance change rate or maximum absorbance change rate, for example.

B. the amount of particles agglutinated by an antigen-antibody reaction. This can be calculated from a change in absorbance, for example.

C. the reaction rate calculated from the change rate of the maximum resonance angle of surface plasmon resonance.

The present invention will be described in detail below, taking as an example the immunoassay according to the above <3> as immunoassay and of the case where the reaction rate of particle agglutination caused by an antigen-antibody reaction is measured as reactivity.

[Immunoassay 1]

The first method of immunoassay of the present invention comprises the standard reaction step of reacting a standard sample containing an object of measurement in a certain concentration with an immuno-reagent in a reaction solution, the specimen reaction step of mixing and reacting the reaction solution of the standard reaction step with a specimen, and the step of determining the concentration of the object of measurement contained in the specimen by comparing the reactivity of the standard reaction step with the reactivity of the specimen reaction step.

<Measurement of Specimen>

(1) Standard Reaction Step

A reaction buffer solution containing an antigen (object of measurement) in a certain concentration (standard sample) and an immuno-reagent obtained by immobilizing an antibody to insoluble carrier particles are added to a reaction vessel and stirred to react the standard sample with the immuno-reagent for a certain time.

(2) Specimen Reaction Step

A specimen is added to the same reaction vessel, mixed with the reaction solution of the above standard reaction step and reacted for a certain period of time.

Absorbance is measured at least before and after each reaction of the standard reaction step and the specimen reaction step to measure agglutination caused by an antigen-antibody reaction.

(3) Calculation of Concentration of Object of Measurement Contained in Specimen

The reaction rate of the standard reaction step (V1) and the reaction rate of the specimen reaction step (V2) are calculated as an average absorbance change rate (change of absorbance/reaction time) calculated from absorbance measured before and after respective reactions.

Thereafter, the ratio (V2/V1) of the reaction rate of the specimen reaction step (V2) to the reaction rate of the standard reaction step (V1) is calculated.

The concentration of the object of measurement contained in the specimen is calculated using the previously prepared calibration curve and the above ratio (V2/V1).

<Preparation of Calibration Curve>

The same reactions as in the above measurement of the specimen are carried out except that a standard reagent containing the object of measurement in a certain concentration is added in place of the specimen to calculate the ratio (V2/V1) of the reaction rate of the latter standard reaction step (second standard reaction step) (V2) to the reaction rate of the first standard reaction step (V1).

The same reactions are repeated by changing the concentration of the standard sample to be added in the second standard reaction.

A calibration curve is prepared with the determined ratio (V2/V1) of the reaction rates and the concentration of the object of measurement contained in the standard sample of the second standard reaction.

According to this method, very accurate measurement results can be obtained without correcting the previously prepared calibration curve.

In the above method, the ratio (V2/V1) of the reaction rates is used for the comparison of reactivity in the above description but the difference of reaction rate (V1–V2) and various operation results using V1 and V2 may be used.

In the above method, the specimen reaction step is carried out after the standard reaction step. However, the order may be reversed and the standard reaction step may be carried out after the specimen reaction step. That is, the specimen and the immuno-reagent are reacted with each other in a reaction solution (specimen reaction step), and then the reaction solution of the specimen reaction step and a standard sample containing the object of measurement in a certain concentration are mixed and reacted with each other (standard reaction step), and the reactivity of the standard reaction step and the reactivity of the specimen reaction step are compared with each other to determine the concentration of the object of measurement contained in the specimen. However when the concentration of the object of measurement contained in the specimen is low, it is recommended to carry out the specimen reaction step after the standard reaction step to achieve high measurement accuracy.

As for the reaction time of each reaction, generally speaking, the reaction time of the first reaction step is 1 second to 10 minutes and the reaction time of the subsequent reaction step is 10 seconds to 1 hour. Preferably, the reaction time of the first reaction step is 1 to 5 minutes and the reaction time of the next reaction step is 1 to 15 minutes.

[Immunoassay 2]

The second method of immunoassay of the present invention for measuring the concentration of the object of measurement contained in the specimen by means of an immuno-reagent comprising an antigen or antibody for the object of measurement comprises a standard reaction step of reacting a standard sample containing the object of measurement in a certain concentration with the immuno-reagent in a reaction solution, the specimen reaction step of mixing and reacting the reaction solution of the standard reaction step with the specimen, the step of correcting the previously prepared calibration curve with the reactivity of the standard reaction step and the step of determining the concentration of the object of measurement contained in the specimen from the corrected calibration curve and the reactivity of the specimen reaction step.

This method of immunoassay is the same as the above method of immunoassay 1 in reaction procedure but differs from the above immunoassay 1 in data processing.

<Measurement of Specimen>

(1) Standard Reaction Step

A reaction buffer solution containing an antigen (object of measurement) in a certain concentration (standard sample) and an immuno-reagent obtained by immobilizing an antibody to insoluble carrier particles are added to a reaction vessel and stirred to be reacted with each other for a certain period of time.

(2) Specimen Reaction Step

A specimen is added to the above reaction vessel, mixed with the reaction solution of the standard reaction step and reacted for a certain period of time.

Absorbance is measured at least before and after each reaction of the standard reaction step and the specimen reaction step to measure agglutination caused by an antigen-antibody reaction.

The reaction rate of the standard reaction step (V1) and the reaction rate of the specimen reaction step (V2) are calculated as an average absorbance change rate (change of absorbance/reaction time) calculated from the absorbance measured before and after respective reactions.

(3) Correction of Calibration Curve

The previously prepared calibration curve below is corrected using the reaction rate of the standard reaction step for the measurement of the specimen (V1).

The correction of the calibration curve is carried out by comparing the reaction rate of the standard reaction step for the measurement of the specimen (V1) with the reaction rate of the first standard reaction step for assay which is carried out for the following calibration (V1). For example, the difference or ratio of the two V1's is used to correct the calibration curve.

When a plurality of assays are performed for preparation of a calibration curve, as the reaction rate of the standard reaction step (V1) used for correcting the calibration curve, a rate of the standard reaction step of one of the assays may be used. Preferably the average of the reaction rate of the standard reaction steps of all assays may be used.

(4) Calculation of Concentration of Object of Measurement Contained in Specimen

The concentration of the object of measurement contained in the specimen is calculated from the corrected calibration curve and the reaction rate of the specimen reaction step (V2).

<Preparation of Calibration Curve>

The same reactions as in the above measurement of the specimen are carried out except that a standard reagent containing the object of measurement in a certain concentration is added in place of the specimen.

The same reactions are repeated by changing the concentration of the standard sample to be added in the second standard reaction.

A calibration curve is prepared with the reaction rate of the second standard reaction (V2) and the concentration of the object of measurement contained in the standard sample of the second standard reaction.

According to this method, the correction of the previously prepared calibration curve and the measurement of the specimen can be carried out in an 1 pot at the same time, thereby making it possible to save the immuno-reagent and cut out the measurement time and labor.

Like the immunoassay 1, the order of the standard reaction step and the specimen reaction step may be reversed. But when the concentration of the object of measurement contained in the specimen is low, it is preferred to carry out the standard reaction step and then the specimen reaction measurement step.

As for the reaction time of each reaction, generally speaking, the reaction time of the first reaction step is 1 second to 10 minutes and the reaction time of the subsequent reaction step is 10 seconds to 1 hour. Preferably, the reaction time of the first reaction step is 1 to 5 minutes and the reaction time of the next reaction step is 1 to 15 minutes.

[Immunoassay 3]

The third method of immunoassay of the present invention for measuring the concentration of an object of measurement contained in a specimen by means of an immuno-reagent comprising an antigen or antibody for the object of measurement comprises two or more standard reaction steps of mixing and reacting two or more standard samples with a reaction solution containing the immuno-reagent sequentially, a specimen reaction step of mixing and reacting the reaction solution of the last standard reaction step with the specimen, a step of preparating a calibration curve from the reactivity of each standard reaction step, and a step of determining the concentration of the object of measurement contained in the specimen by using the calibration curve and the reactivity of the specimen reaction step, wherein at least the standard samples of a second or later standard reaction steps contain the object of measurement in a certain concentration.

Since this immunoassay enables calibration and the measurement of the specimen to be carried out at the same time by one time of measurement, the time and labor for calibration can be cut out and accurate measurement results can be obtained.

<Measurement of Specimen>

(1) Standard Reaction Step

1. First Standard Reaction Step

A reaction buffer solution containing an antigen (object of measurement) in a certain concentration (standard sample 1) and an immuno-reagent obtained by immobilizing an antibody to insoluble carrier particles are added to a reaction vessel and stirred to be reacted with each other for a certain period of time. It is desired that the concentration of the object of measurement contained in the standard sample 1 is "0". However the standard sample may contain the object of measurement.

2. Second Standard Reaction Step

A standard sample 2 is added to the above reaction vessel, and the reaction solution of the above first standard reaction step and the standard sample 2 are mixed and reacted with each other for a certain period of time.

The additional standard reaction step may be carried out with the above procedure one or more times by adding the object of measurement contained in the standard sample.

As for the reaction time of each reaction, generally speaking, it is 1 second to 10 minutes and preferably 1 to 5 minutes. The reaction time of each reaction steps may be the same or different.

The number of standard reaction steps is generally 2 or 3 in total. Since the standard samples are added to the same reaction vessel in the standard reaction steps, when the concentration of an i-th standard sample of the i-th standard reaction step is denoted by Ci, the standard sample with the concentration expressed by $$\sum_{i=1}^{n} Ci$$

could be considered to be added to the immuno-reagent in the n-th standard reaction step.

Strictly speaking, the correction of the volume of the standard sample is necessary. However, when the volume of the standard sample added is smaller than the total volume of the reaction solutions, the correction is not necessary.

After the end of the standard reaction step, the specimen whose concentration is unknown is added to carry out the specimen reaction step. To take as wide a measurable region for the concentration of the specimen as possible, $$\sum_{i=1}^{n} Ci$$

must be controlled to an appropriate concentration or less in the measurable range of the measurement item. Stated more specifically, in general immunoassay, the relationship between the concentration of the object of measurement and reactivity, which differs according to the object of measurement and measurement method, is like a sigmoid curve in most cases. It is desired to set $$\sum_{i=1}^{n} Ci$$

to a value which falls within a concentration region that can ensure a accurate quantitative measurement in the sigmoid curve.

(2) Specimen Reaction Step

The specimen is added to the same reaction vessel, mixed with the reaction solution of the above standard reaction step and reacted for a certain period of time (specimen reaction step).

Absorbance is measured at least before and after each reaction of the standard reaction step and the specimen reaction step to measure agglutination caused by an antigen-antibody reaction.

(3) Preparation of Calibration Curve

A calibration curve is prepared with the concentration of the object of measurement contained in the standard sample and the reaction rate of each standard reaction step.

Since the standard samples are added to the same reaction vessel in the standard reaction steps, when the concentration of an i-th standard sample of the i-th standard reaction step is denoted by Ci, the standard sample with the concentration expressed by $$\sum_{i=1}^{n} Ci$$

could be considered to be added to the immuno-reagent in the n-th standard reaction step.

Thus, the calibration curve is prepared by carrying out, for example, linear regression, quadric curve regression or Log-Logit regression with "n" sets of data (C1, V1), $$\left(\sum_{i=0}^{2} Ci, V2\right), ... \left(\sum_{i=1}^{n} Ci, Vn\right)$$

on the concentration and the reaction rate of each standard reaction step.

(4) Calculation on Concentration of Object of Measurement Contained in Specimen

When the concentration of object of measurement contained in the specimen is C, the standard sample with the concentration expressed by $$C + \sum_{i=1}^{n} Ci$$

could be considered to be added to the immuno-reagent in the specimen reaction step.

Thus, the concentration of the object measurement contained in the specimen expressed by $$C + \sum_{i=1}^{n} Ci$$

could be determined by extrapolating the reaction rate of the specimen reaction step and the above calibration and substracting $$\sum_{i=1}^{n} Ci$$

from obtained value.

With the proviso that in this case of $$C + \sum_{i=1}^{n} Ci$$

and $$\sum_{i=1}^{n} Ci,$$

concentrations do not need to be corrected by volume such as the quantity of the reaction solution, added standard samples or added specimen samples.

Known immuno-reagents or the like may be used as the immuno-reagent used in the immunoassay of the present invention. For example, the following can be used in the immunoassay according to the above <3>.

Examples of the material of the insoluble carrier particles used in the immuno-reagent include organic polymers obtained by emulsion polymerizing polymers or copolymers consisting of styrene, vinyl toluene, methyl methacrylate and methacrylic acid or the like; substances derived from a living body such as a red blood cell; metal colloidal particles such as gold colloid; lipid particles such as liposome; and inorganic particles such as silica. The particle size of the insoluble carrier particles is generally 0.01 to 10 μm, preferably 0.1 to 1 μm.

The amount of the antibody or antigen immobilized to the insoluble carrier particles is generally 50 ng to 500 μg, preferably 500 ng to 200 μg based on 1 mg of the insoluble carrier particles. To immobilize the antibody or antigen, known methods such as a physical adsorption method and chemical binding method using a condensing agent such as carbodiimide may be used.

As for the concentration of the insoluble carrier particles, the weight concentration of the insoluble carrier particles in the immunoreaction solution is generally 0.0001 to 1%, preferably 0.0003 to 0.3%.

Examples of a dispersion medium for dispersing the insoluble carrier particles include water; buffer solutions such as trishydroxymethyl aminomethane and phosphoric acid (generally 1 to 500 mM, generally pH of 5 to 10, preferably 6 to 9); what contains 0.01 to 10% of a component derived from a living body such as bovine serum albumin or gelatin; what contains 0.1 to 10% of a salt such as sodium chloride; what contains 0.0001 to 1% of a surfactant (nonionic, anionic, cationic or amphoteric); and a combination thereof.

As the reaction buffer solution, there can be mentioned of what contains an inorganic salt such as sodium chloride (0.5 to 20%), 0.1 to 10% of a biocomponent such as bovine serum albumin or normal rabbit serum and 0.0003 to 1% of a surfactant in a buffer solution such as trishydroxymethyl aminomethane, phosphoric acid, sodium acetate, glycin or boric acid (1 to 500 mM, pH of 1 to 10).

There are two cases according to a reaction system: one case where only one reaction buffer solution is used and the other case where two or more different buffer solutions are used. When one reaction buffer solution is used, the neutral pH of 6 to 9 is used in most cases.

The concentration of a salt and the concentration of a protein are suitably adjusted according to the reaction system.

Known apparatuses may be used in the immunoassay of the present invention. A description is subsequently given of the apparatus used in the immunoassay according to the above <3>.

FIG. 1 shows a test kit used in the present invention and comprising an immuno-reagent holder 1 for storing an immuno-reagent, standard sample holders 2 for storing respective standard samples, a specimen holder 3 for a specimen being injected, and a reaction vessel 4. The standard sample holders are provided corresponding to the required number of standard samples. When it is not preferred to dilute the immuno-reagent with a buffer solution for storage, and the immuno-reagent and the buffer solution are preferred to be mixed together at the time of a reaction, a buffer solution holder 5 is further provided to store the immuno-reagent and the buffer solution separately.

Figure 2:
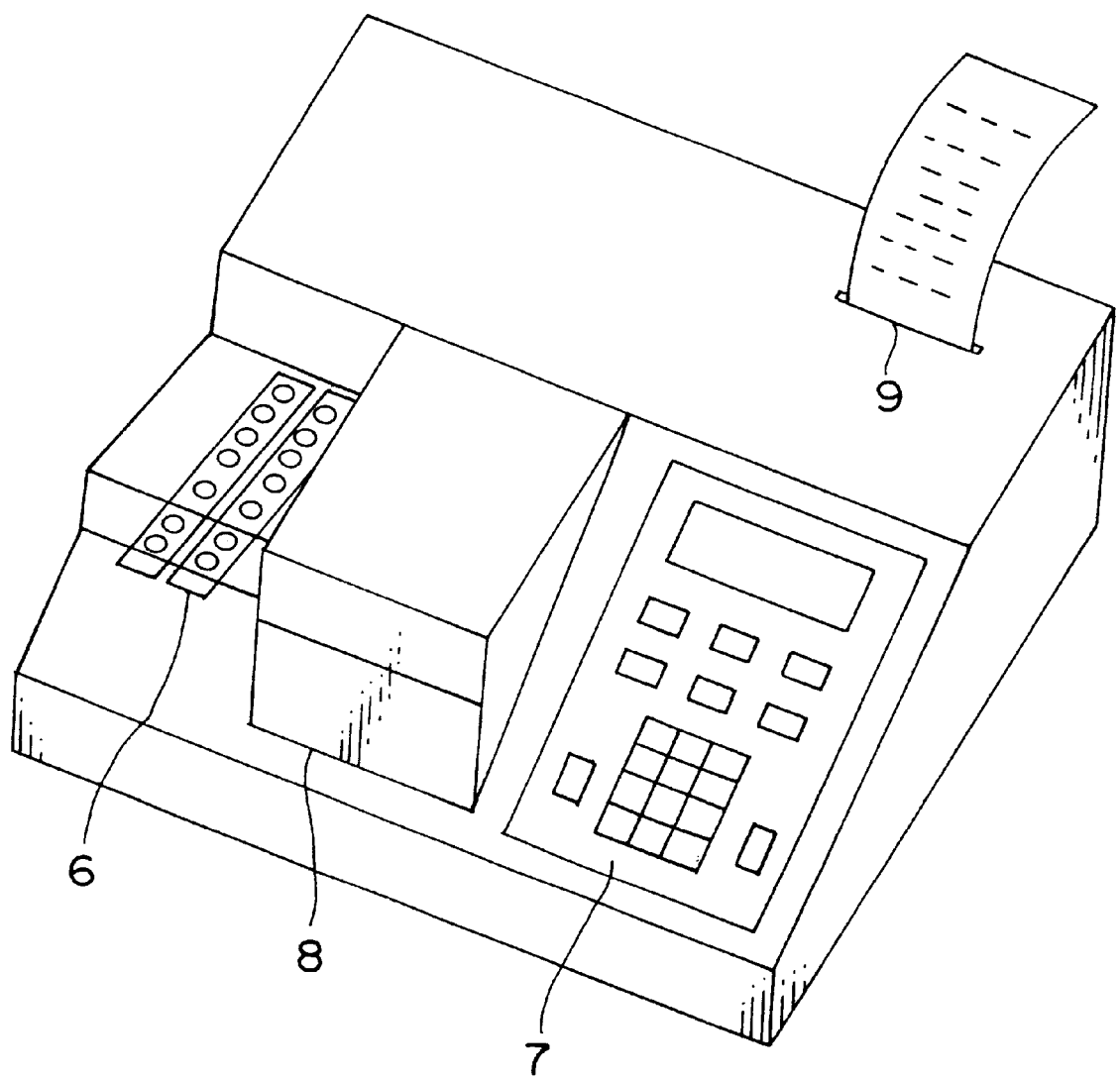
FIG. 2 shows an immunoassay apparatus used in the present invention.

This test kit is set in a test kit container 6 of the immunoassay apparatus of FIG. 2. The immunoassay apparatus of FIG. 2 comprises the container 6 for the immunoassay test kit shown in FIG. 1, means of operating a standard reaction between a standard reagent and an immuno-reagent, means of operating a specimen reaction between a specimen and the immuno-reagent, means of measuring the state of a reaction solution at least before and after each reaction of the standard reaction and the specimen reaction, means of determining the concentration of an object of measurement contained in the specimen by processing measurement data determined by the standard reaction and the specimen reaction and pre-read calibration curve data, and means of displaying the determined concentration of the object of measurement contained in the specimen.

Figure 3:
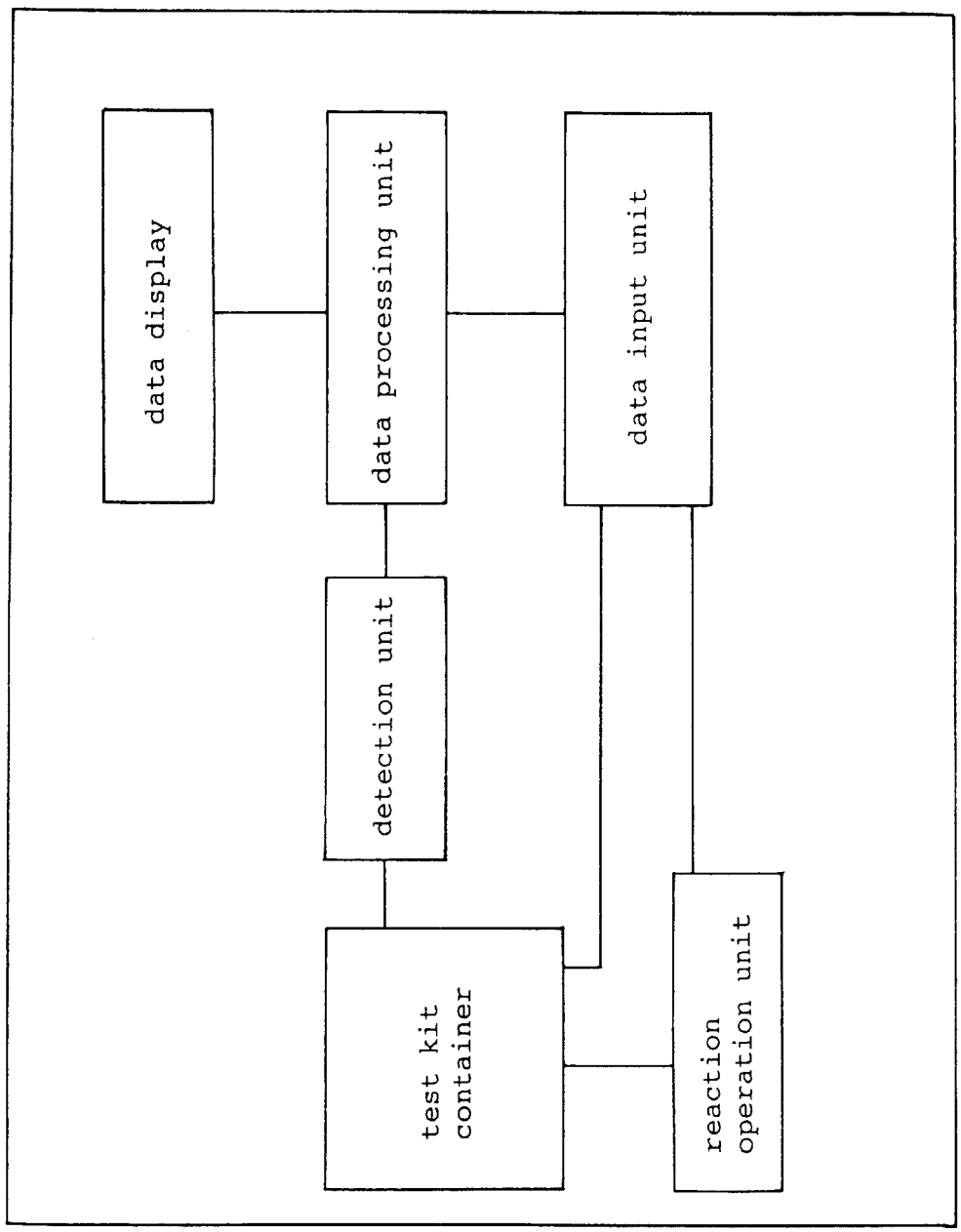
FIG. 3 shows a conceptual diagram of an immunoassay apparatus used in the present invention.
Figure 4:
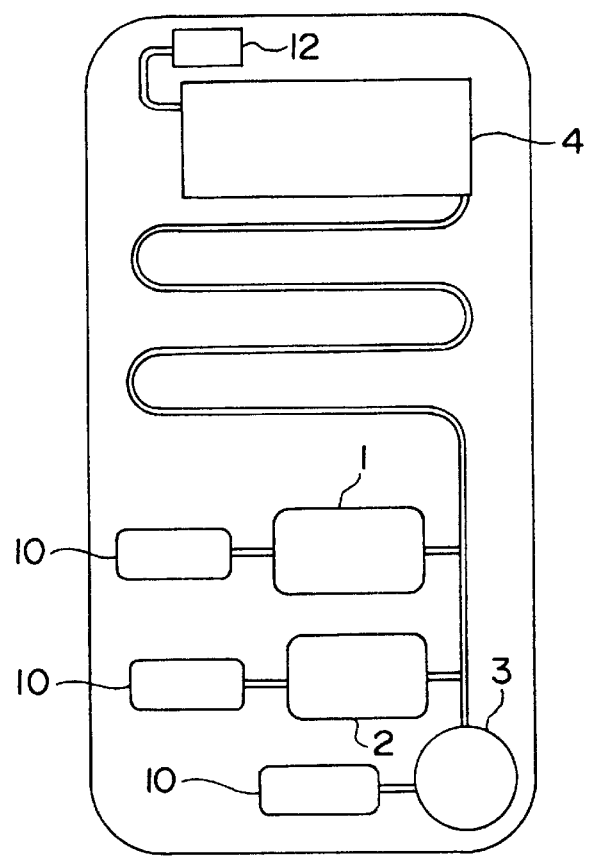
FIG. 4 shows a test kit used in the first or second immunoassay of the present invention.
Figure 5:
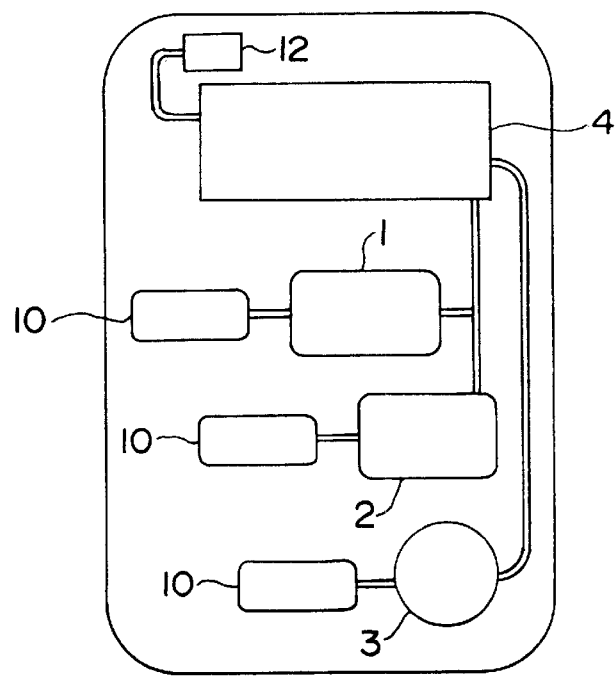
FIG. 5 shows a test kit used in the first or second immunoassay of the present invention.

FIG. 3 shows a schematic diagram of the immunoassay apparatus. The measurement operation will be described with reference to FIGS. 2 and 3. As for operation procedure, the test kit of FIG. 1 is first set in the test kit container 6 and the specimen is injected into the specimen holder 3 of the test kit. Measurement conditions are input into a data input unit by inputting into an input panel,or by reading bar codes or the like printed on a test cassette. When the measurement is started, a reaction operation unit carries out a reaction operation according to the measurement conditions input into the data input unit. The reaction operation unit injects the immuno-reagent, standard sample, specimen and the like of the reagent kit from a sample nozzle provided in the apparatus into the reaction vessel sequentially and causes them to react with one another by mixing them with mixing nozzle provided in the apparatus. The state (such as absorbance) of the reaction solution is measured by a detection unit 8. The state of the reaction solution is measured at least before and after each reaction. In the above immunoassays 1 and 2, the data input unit reads calibration curve data printed in the form of bar codes or the like on the reagent kit, a data processing unit calculates the concentration of the object of measurement contained in the specimen from the calibration curve data and the measurement data, and a data display unit 9 displays the results or outputs paper printed with the results. In the above immunoassay 2, the data (V1) required for correcting the calibration curve may be printed on the test cassette and the data may be used for data processing. In the above immunoassay 3, the data processing unit draws a calibration curve from the measurement data and calculates the concentration of the object of measurement contained in the specimen, and the data display unit 9 displays or outputs the results.

Figure 6:
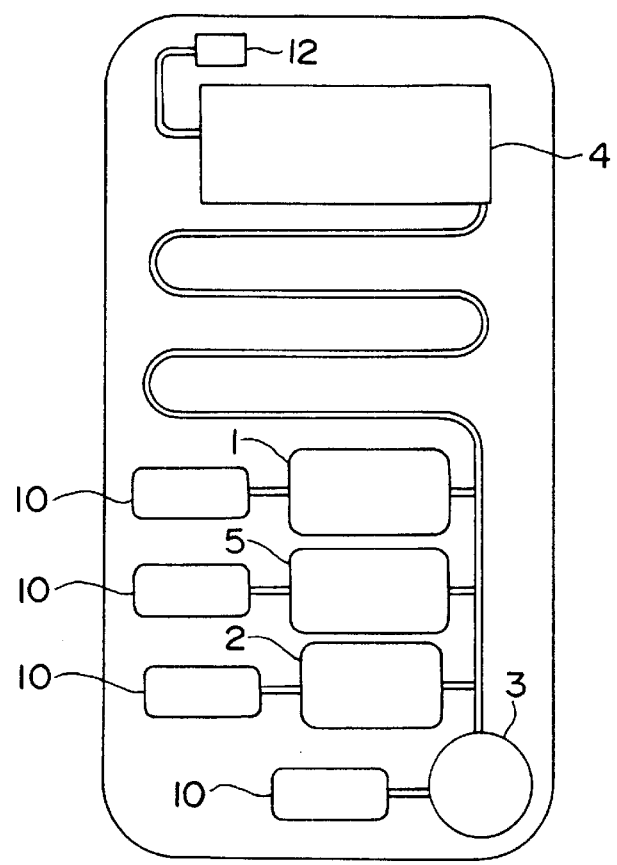
FIG. 6 shows a test kit used in the first or second immunoassay of the present invention.
Figure 7:
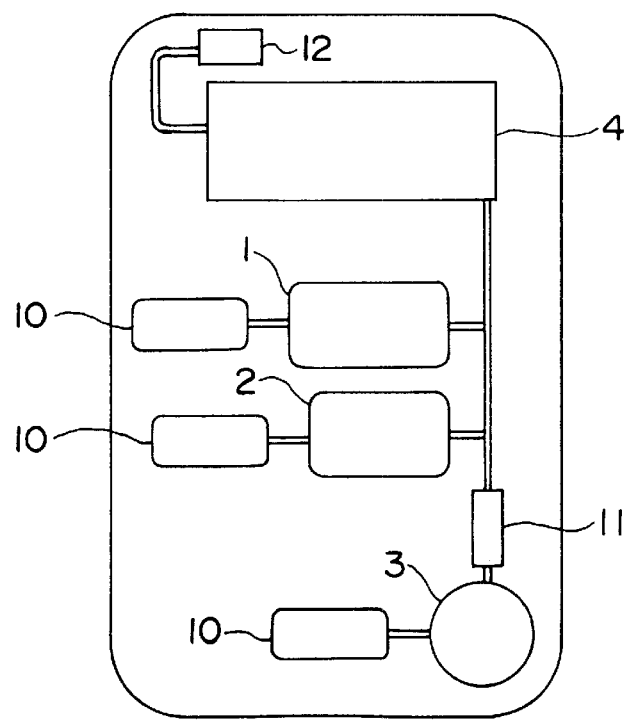
FIG. 7 shows a test kit used in the first or second immunoassay of the present invention.
Figure 8:
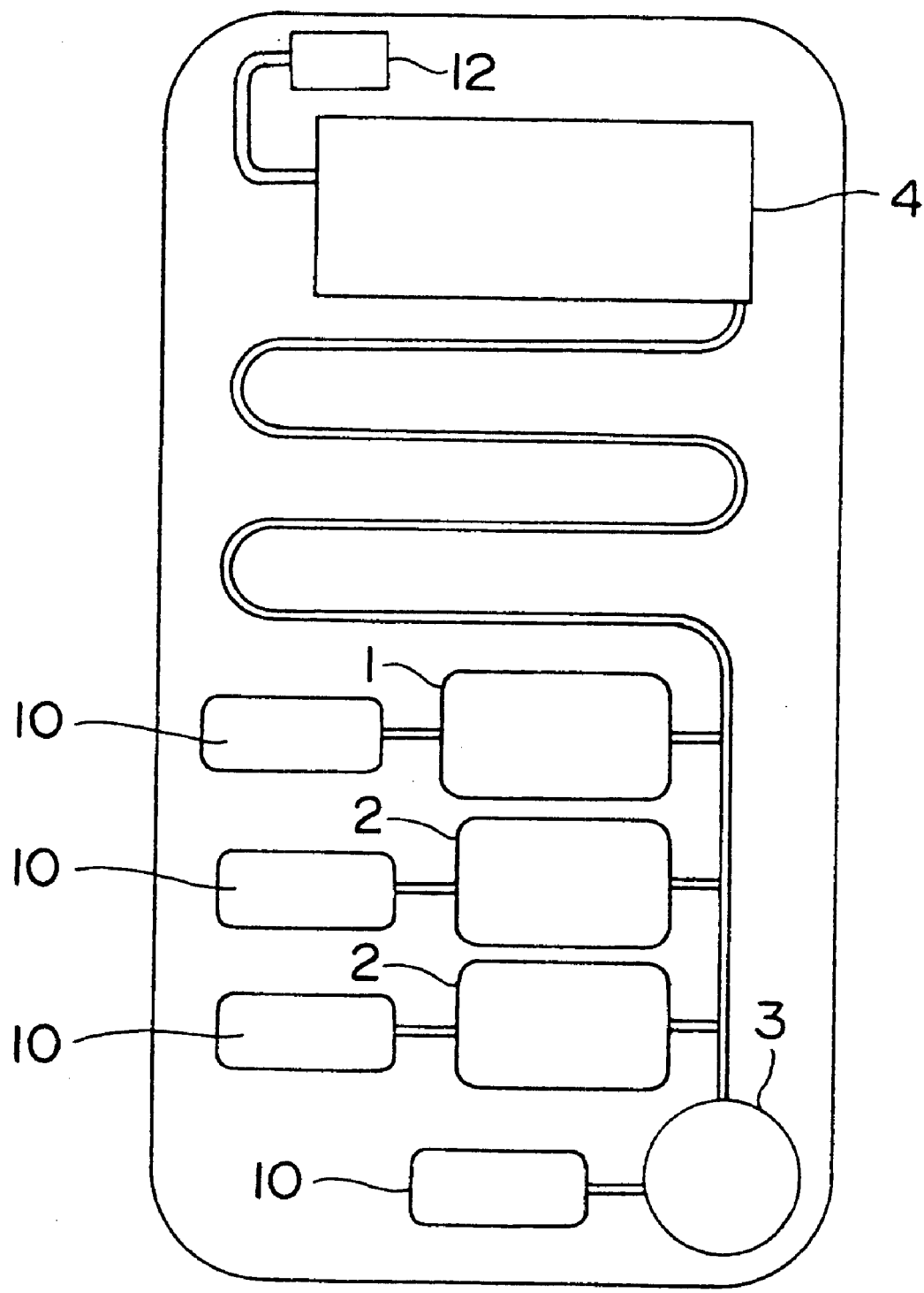
FIG. 8 shows a test kit used in the third immunoassay of the present invention.
Figure 9:
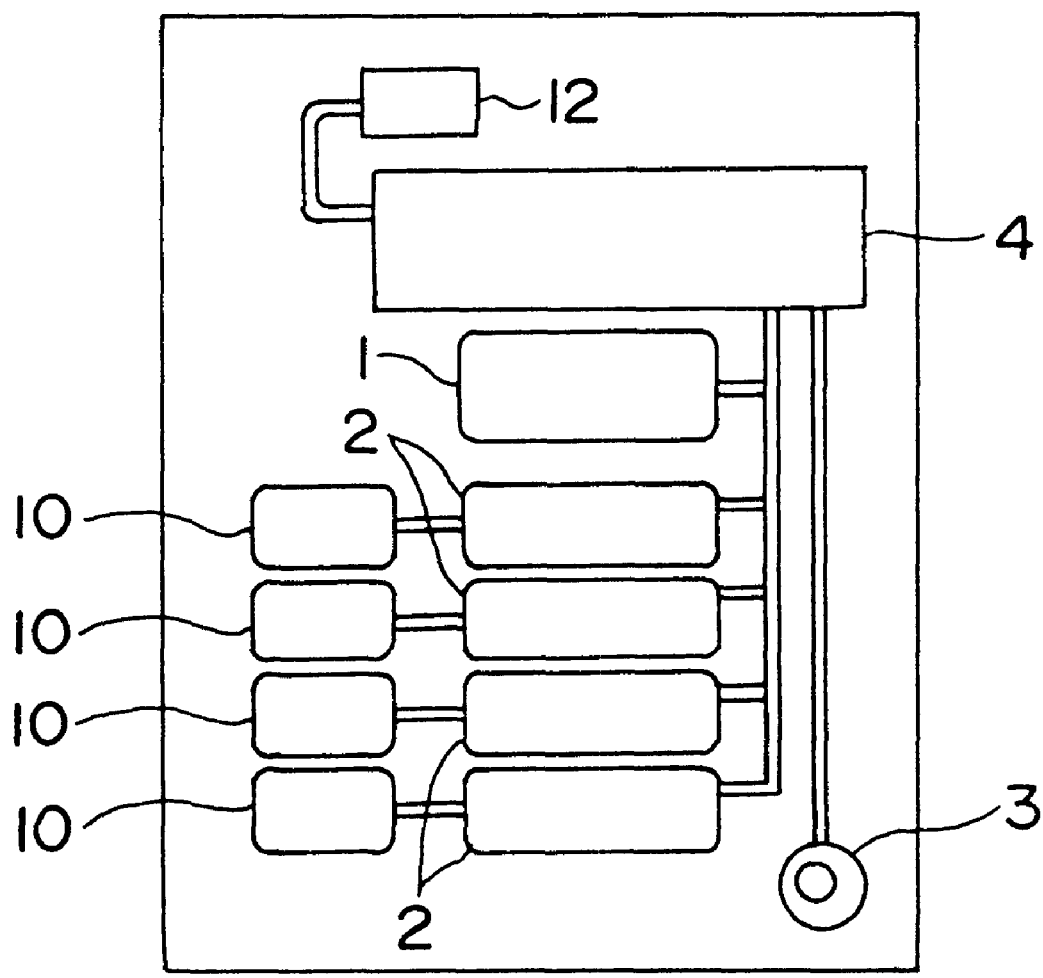
FIG. 9 shows a test kit used in the third immunoassay of the present invention.

The test kit may be a test kit comprising a substrate carrying thereon the immuno-reagent holder, the standard sample holder and the specimen holder which are communicated to the reaction vessel by pipes and arranged on the same substrate (FIGS. 4 to 9). As a unit for supplying the immuno-reagent, the standard sample or the specimen into the reaction vessel, for example, each extrusion air layer 10 is formed in the immuno-reagent holder, the standard sample holder and the specimen holder. In this case, according to reaction conditions input into the apparatus in advance, each air layer is compressed by the reaction operation unit in the measurement apparatus sequentially so that the immuno-reagent, the standard sample and the specimen are supplied into the reaction vessel one after another. The extruded air or liquid are collected into a waste stowage 12. The waste stowage may have an air hole. In the case of the above immunoassays 1 and 2, the test kits of FIGS. 4 to 7 can be used. When it is not preferred that the immuno-reagent be stored in a diluted state with a buffer solution, and the immuno-reagent and the buffer solution are to be stored separately, the reagent kit of FIG. 6 is used. When blood corpuscles contained in the specimen are to be separated before a reaction, as shown in FIG. 7, a blood separation filter 11 is preferably interposed between the specimen holder and the reaction vessel. In the case of the above immunoassay 3, test chips having two or more standard sample holders shown in FIGS. 8 and 9 may be used. The standard sample holders are provided corresponding to the required number of standard samples.

The immunoassay according to the above <3> has been described above as an example. An example where the immunoassay according to the above <11> is used will be described hereinafter.

In a reaction vessel having a gold substrate in a lower portion thereof, an antibody is bound to the gold substrate. Methods for binding the antibody to the substrate include one in which an antibody is physically adsorbed to a substrate, one in which an antibody is chemically bound to the molecule of dextran or polyethylene glycol which are physically adsorbed to a substrate, and one in which a reagent for self-assembled monolayers having a thiol group is bound to a substrate and a functional group such as a carboxyl group existent in the formed self-assembled monolayers and an antibody molecule are chemically bonded to each other, or the like.

For example, in the above immunoassay 1, the antibody on the substrate and a standard antigen product having a certain concentration are caused to react with each other in a reaction buffer solution (standard reaction step) and then the reaction solution of the standard reaction step and a specimen are mixed and reacted with each other (specimen reaction step). During each reaction, the reaction vessel is illuminated from below to measure surface plasmon resonance. Along with the proceeding of an antigen-antibody reaction, the maximum resonance angle changes or maximum resonance absorption wavelength shifts. The reaction rate is calculated from the change rate. The ratio of the reaction rate of the standard reaction step to the reaction rate of the specimen reaction step is calculated and the concentration of the object of measurement contained in the specimen is calculated from the previously prepared calibration curve.

EXAMPLES

The following examples are provided for the purpose of further illustrating the present invention but are in no way to be taken as limiting.

EXAMPLES 1

The LPIA-A700 (Mitsubishi Chemical Corp.) was used as an immunoassay apparatus. 0.5 mg of an anti-α-fetoprotein (AFP) antibody (Rabbit F(ab')$_2$) was immobilized to 10 mg of polystyrene latex particles by chemical binding and diluted with 10 ml of a Tris buffer solution containing 0.1% of bovine serum albumin (BSA) (Sigma) to prepare a latex reagent for measuring AFP.

<Measurement of Specimen>

(1) Standard Reaction Step

20 µl of a standard sample (20 ng/ml) obtained by diluting AFP with a 0.1% BSA-containing Tris buffer solution, 150 µl of a 0.1% BSA-containing Tris buffer solution, 100 µl of the previously prepared latex reagent for measuring AFP and 30 pl of water were added to a reaction vessel and stirred to observe changes in the absorbance of light having a wavelength of 800 nm for 7 minutes so as to determine reaction rate 1 (V1). The reaction rate was determined as the average rate of absorbance change. (2) specimen reaction step Subsequently, 20 μl of a serum as a specimen was added to the same reaction vessel and stirred to observe changes in the absorbance of light having a wavelength of 800 nm for 10 minutes so as to determine reaction rate 2 (V2) and calculate the ratio of reaction rates (V2/V1). Twelve specimens were measured with the same procedure.

<Preparation of Calibration Curve>

Figure 10:
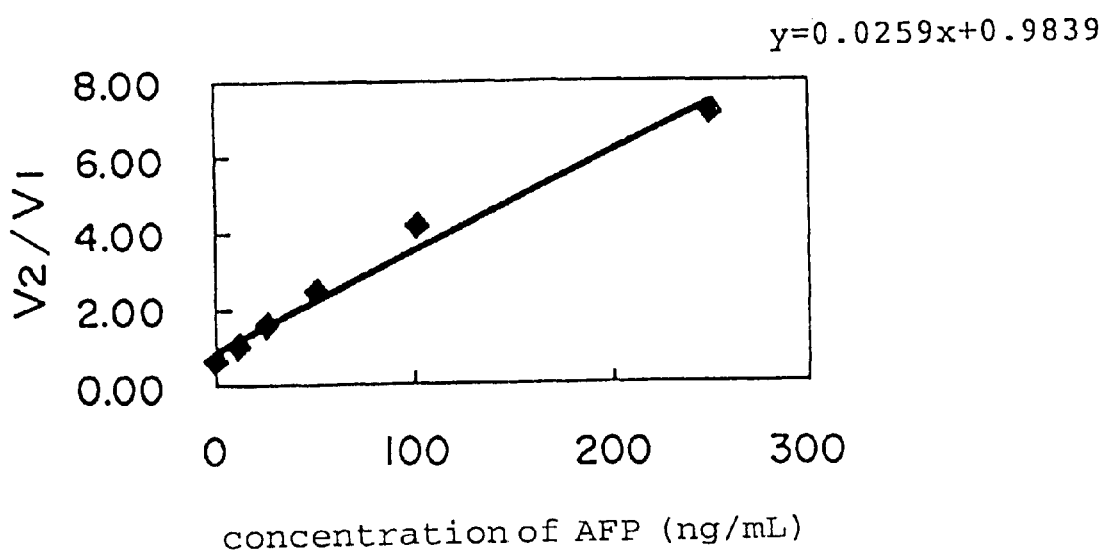
FIG. 10 shows a calibration curve obtained in Example 1.

A reaction was carried out under the same conditions as in the above measurement of the specimen except that a standard sample (0, 10, 25, 50, 100 or 250 ng/ml) was added in place of the specimen to determine the ratio of reaction rates (V2/V1) from each reaction rate. A calibration curve was prepared from the concentration (0, 10, 25, 50, 100 or 250 ng/ml) of AFP contained in the standard sample used in the second standard reaction and the ratio of the reaction rates (V2/V1). The results are shown in FIG. 10. It is understood from FIG. 10 that a satisfactory calibration curve was prepared.

The concentration of AFP contained in the serum of the specimen was calculated from this calibration curve and the measurement results of the specimen. The results are shown in Table 1.

Comparative Example 1

To confirm the accuracy of measurement of the concentration of AFP in specimen by the above method of the present invention, measurement was made by the conventional latex agglutination immuno reaction method as a control immunoassay. The reaction buffer solution (latex reagent for measuring AFP), 0.1% BSA-containing Tris buffer solution, AFP standard sample and specimen used in Example 1 were used for the measurement.

<Preparation of Calibration Curve>

Figure 11:
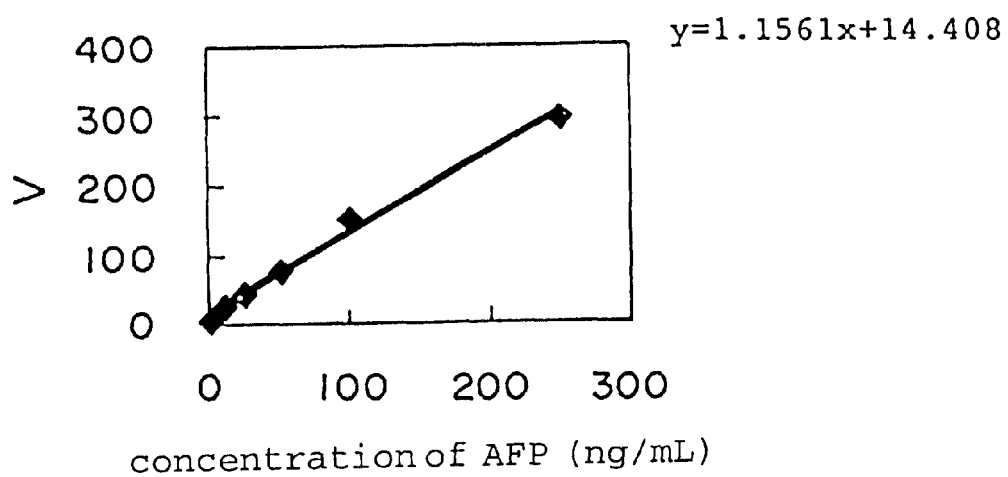
FIG. 11 shows a calibration curve obtained in Comparative Example 1.

To a reaction vessel, 20 μl of an AFP standard sample (0, 10, 25, 50, 100 or 250 ng/ml), 30 μl of water, 150 μl of a reaction buffer solution and 100 μl of a latex reagent for measuring AFP were added, and stirred to observe changes in the absorbance of light having a wavelength of 800 nm for 10 minutes so as to determine reaction rate (V). The reaction rate was calculated as the average rate of absorbance change The relationship between the AFP concentration of the standard sample and the reaction rate (V) is shown in FIG. 11. It is understood from FIG. 11 that a satisfactory calibration curve was prepared.

<Measurement of Specimen>

Subsequently, the same reaction as in the above measurement of the AFP standard sample was carried out except that the specimen was added in place of the AFP standard sample to calculate the reaction rate (V) and the concentration of AFP contained in the specimen using the previously prepared calibration curve. The results are shown in Table 1.

TABLE 1

| Specimen | Comparative Example 1 (ng/mL) | Example 1 (ng/mL) |
|---|---|---|
| 1 | 7.1 | 11.9 |
| 2 | 16.2 | 17.6 |
| 3 | 18.6 | 24.6 |
| 4 | 44.9 | 42.8 |
| 5 | 15.1 | 12.5 |
| 6 | 19.8 | 19.2 |
| 7 | 52.9 | 44.6 |
| 8 | 78.9 | 71.2 |
| 9 | 96.4 | 89.3 |
| 10 | 120.4 | 113.9 |
| 11 | 150.8 | 142.9 |
| 12 | 153.7 | 141.1 |

Figure 12:
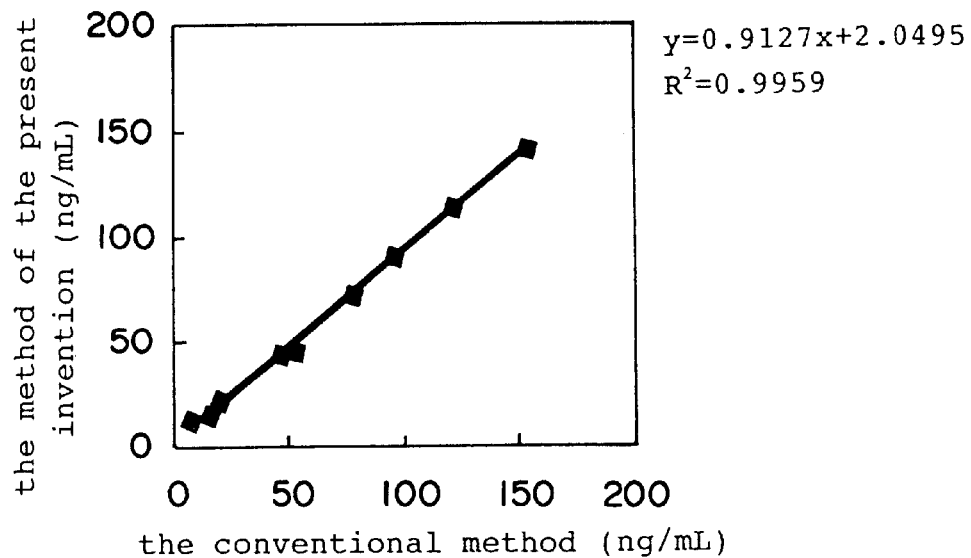
FIG. 12 is a diagram showing the correlation between the concentration of AFP in twelve specimen measured by Example 1 and the concentration measured by Comparative Example 1.

FIG. 12 shows a correlative diagram of Example 1 and Comparative Example 1. The correlation was satisfactory with $Y=0.9127X+2.0495$ and $R^2=0.9959$. Thereby, the results obtained by measuring with the conventional latex agglutination immunoassay and the results obtained by measuring with the immunoassay of the present invention show extremely good correlation. That is, it is possible to measure the concentration of AFP contained in the serum by the immunoassay of the present invention.

Example 2

LPIA-A700 (Mitsubishi Chemical Corp.) was used as an immunoassay apparatus.

0.5 mg of an anti- AFP antibody (Rabbit F(ab')$_2$) was immobilized to 10 mg of polystyrene latex particles by chemical binding and diluted with 10 ml of a 0.1% BSA-containing Tris buffer solution to prepare six different latex reagents for measuring AFP by changing the production lot.

<Measurement of Specimen>

(1) Standard Reaction Step

20 μl of a standard sample (20 ng/ml AFP) obtained by diluting AFP with a 0.1% BSA-containing Tris buffer solution, 150 μl of a 0.1% BSA-containing Tris buffer solution (reaction buffer solution), 100 μl of the previously prepared latex reagent for measuring AFP and 30 μl of water were added to a reaction vessel and stirred to observe changes in the absorbance of light having a wavelength of 800 nm for 7 minutes so as to determine reaction rate 1 (V1). The reaction rate was determined as the average rate of absorbance change.

(2) Specimen Measurement Step

Subsequently, 20 μl of a serum as a specimen was added to the same reaction vessel and stirred to observe changes in the absorbance of light having a wavelength of 800 nm for 10 minutes so as to determine reaction rate 2 (V2).

Two different specimens (K, S) were measured. The same specimen was measured six times by changing the production lot of the latex reagent for measuring AFP.

<Preparation of Calibration Curve>

The ratio of the reaction rates (V2/V1) was determined by measuring in the same manner as in the above measurement of the specimen except that the reagent of the production lot 1 was used as the latex reagent for measuring AFP and an AFP standard sample (0, 10, 25, 50, 100 or 250 ng/ml) was used in place of the specimen to draw a calibration curve.

The concentration of AFP contained in the specimen was calculated from the calibration curve and the measurement results of the specimen measured by changing the production lot of the latex reagent for measuring AFP. The results are shown in Table 2.

Comparative Example 2

Measurement was made by the conventional latex agglutination immuno reaction using six different latex reagents as a control immunoassay. The latex reagent, reaction buffer solution, standard sample and specimen used in Example 2 were used for the measurement.

<Preparation of Calibration Curve>

To a reaction vessel, 20 μl of an AFP standard sample (0, 10, 25, 50, 100 or 250 ng/ml), 150 μl of a 0.1% BSA-containing Tris buffer solution, 30 μl of water and 100 μl of the latex reagent of the production lot 1 were added, and stirred to observe changes in the absorbance of light having a wavelength of 800 nm for 10 minutes so as to determine reaction rate. The reaction rate was determined as the average rate of absorbance change. A calibration curve was prepared from the concentration of AFP contained in the standard sample and the reaction rate.

<Measurement of Specimen>

A reaction was carried out in the same manner as above except that the specimen was added in place of the standard sample. The same specimens (K, S) were measured six times by changing the production lot of the latex reagent. The results are shown in Table 2.

TABLE 2

Example 2 concentration of AFP (ng/ml)

| Reagent lot | K | S |
| --- | --- | --- |
| 1 | 48.51 | 76.27 |
| 2 | 57.04 | 76.29 |
| 3 | 40.75 | 71.28 |
| 4 | 57.21 | 82.56 |
| 5 | 53.94 | 97.23 |
| 6 | 46.32 | 98.11 |
| mean | 50.6 | 83.6 |
| SD | 6.6 | 11.5 |
| CV(%) | 13.0 | 13.7 |

Comparative Example 2 concentration of AFP (ng/ml)

| Reagent lot | K | S |
| --- | --- | --- |
| 1 | 53.55 | 81.81 |
| 2 | 78.10 | 106.67 |
| 3 | 30.88 | 48.30 |
| 4 | 51.58 | 81.45 |
| 5 | 79.23 | 147.67 |
| 6 | 30.11 | 53.00 |
| mean | 53.9 | 86.5 |
| SD | 21.6 | 36.8 |
| CV(%) | 40.0 | 42.6 |

SD: Standard deviation
CV (%): Coefficient of variation (relative standard deviation)

Table 2 shows that CV was 40.0 or 42.6 (%) in the conventional immunoassay and 13.0 or 13.7% in the immunoassay of the present invention when the reagents of six different production lots were used. Variations caused by differences between reagent production lots can be corrected by the immunoassay of the present invention unlike the conventional immunoassay.

Example 3

Measurement was made by turbidimetric immunoassay using LPIA-S500 (Mitsubishi Chemical Corp.) as an immunoassay apparatus.

<Preparation of Calibration Curve>

(1) First Standard Reaction Step

To a reaction vessel, 3 µl of an IgG standard sample (250 mg/dl), 240 µl of a 1:1 mixture of $R_A$ and $R_B$ of an Iatroace IgG reagent (immuno-reagent of Dia-Iatron Co., Ltd.) and 100 µl of water were added, and stirred to observe changes in the absorbance of light having a wavelength of 660 nm for 5 minutes so as to determine reaction rate 1 (V1). The reaction rate was determined as the maximum rate of absorbance change. The IgG standard sample was prepared by diluting a 5,000 mg/dl standard product for Iatroace (Dia-Iatron Co., Ltd.) with a dedicated diluent.

(2) Second Standard Reaction Step

To the same reaction vessel, 20 µl of an IgG standard sample (0, 10, 25, 50, 100, 250 or 500 mg/dl) was added, and stirred to observe maximum in the absorbance of light having a wavelength of 660 nm for 10 minutes so as to determine reaction rate 2 (V2). The reaction rate was determined as the maximum rate of the absorbance change.

Figure 13:
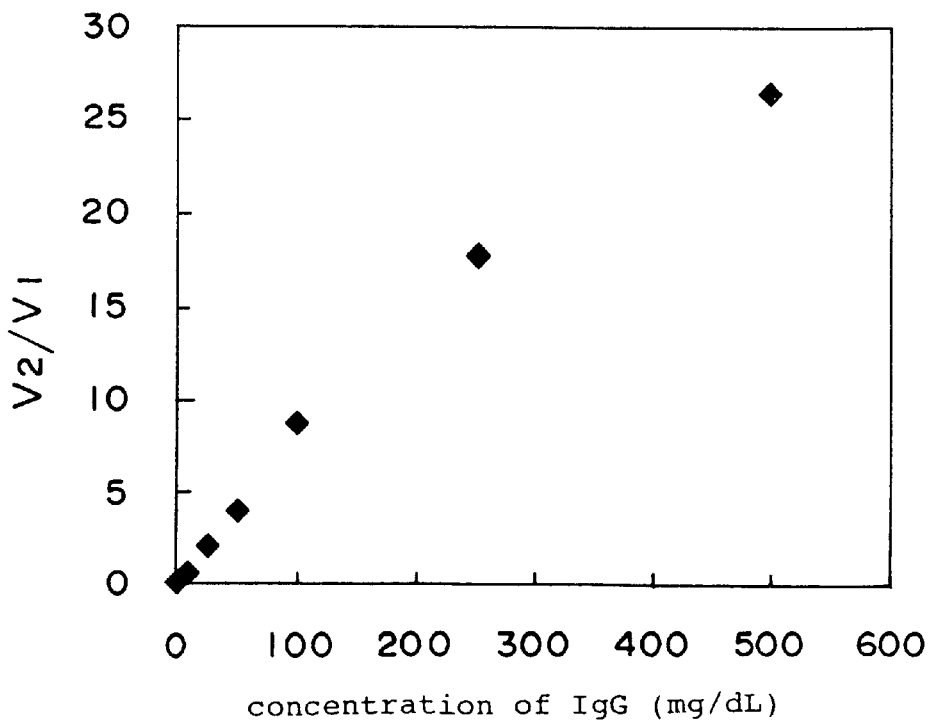
FIG. 13 shows a calibration curve obtained in Example 3.

A calibration curve was prepared from the ratio of the reaction rates (V2/V1) and the IgG concentration of the standard sample of the second standard reaction. The results are shown in FIG. 13. Since a satisfactory calibration curve was obtained, it is understood that the immunoassay of the present invention can be applied to turbidimetric immunoassay.

Example 4

A polarization unit (a device with fluorescence polarization accessory P/N250-0036 for the F-4010 type spectrofluorometer of Hitachi, Ltd.) was set in the F4010 spectrofluorometer (Hitachi) as an immunoassay apparatus.

T3 (3,3',5-triiodothyronine) (Sigma) was labeled with FITC (fluorescein isothiocyanate) (Research Organics) to prepare a fluorescent reagent which is a T3-FITC conjugate.

T3 was diluted with a 0.1% BSA-containing Tris buffer solution to prepare a T3 standard sample (0, 10, 20, 50, 100 or 500 µg/ml).

(1) First Standard Reaction Step

To 300 µl of the FITC labeled T3 (0.14 µlg/ml), 10 µl of the T3 standard sample (200 µg/ml) and 10 µl of an anti-T3 monoclonal antibody (Biospacific) (0.3 mg/ml) were added, and stirred to measure the fluorescence polarization for 1 minute, and the fluorescence polarization after 1 minute of stirring is shown as P1.

(2) Second Standard Reaction

To the same reaction vessel, 10 µl of the T3 standard sample (0, 10, 20, 50, 100, or 500 µg/ml) was added and stirred, and the fluorescence polarization was measured for 4 minutes, and the fluorescence polarization after 4 minutes of stirring is shown as P2.

The fluorescence polarization was measured under a condition that an excitation wavelength is at 495 nm, a fluorescence wavelength is at 529 nm and a polarizer switching time is 10 sec.

Figure 14:
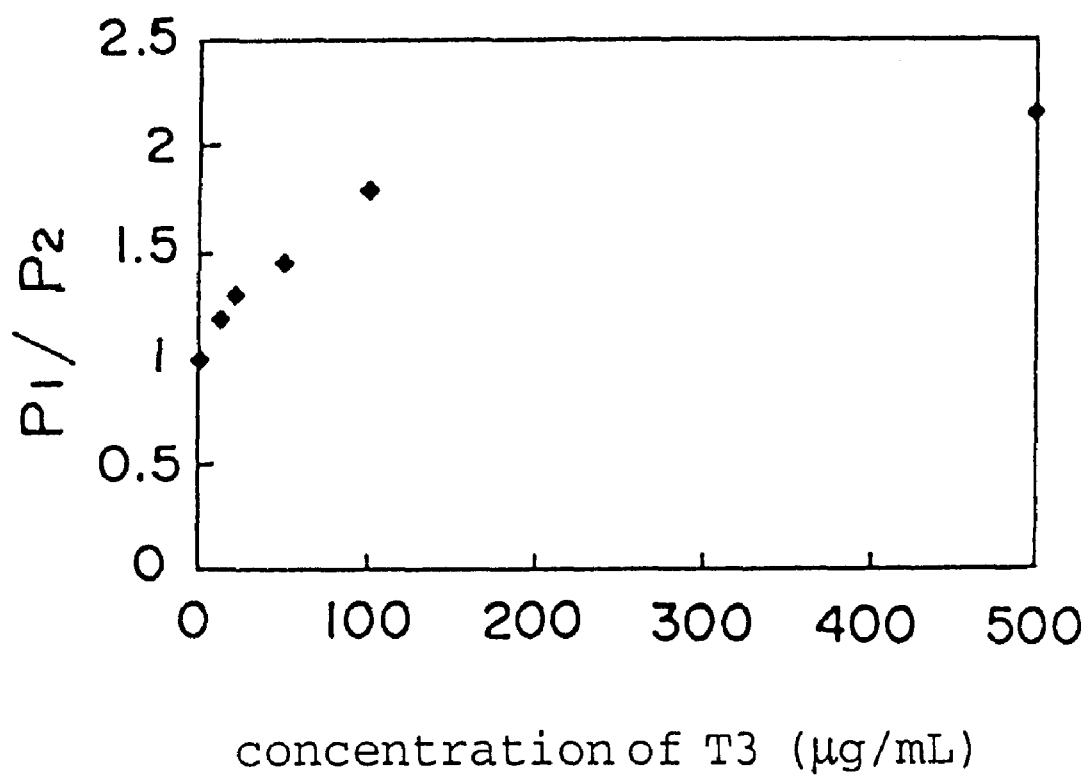
FIG. 14 shows a calibration curve obtained in Example 4.

It was confirmed that a satisfactory calibration curve was obtained from the concentration of T3 and the ratio (P1/P2) of the fluorescence polarizations (FIG. 14). Therefore, it is understood that the immunoassay of the present invention can be applied to fluorescence polarization immunoassay.

The immunoassay of the present invention makes it possible to carry out highly accurate measurement by suppressing a measurement error caused by variations in reaction conditions, to reduce the amount of an immuno-reagent used, and to cut out measurement labor and time.

What is claimed is:

1. An immunoassay method for measuring the concentration of an analyte in a test specimen, using an immunoreagent, wherein one of the analyte or the immunoreagent is an antigen, and the other of the analyte or the immunoreagent is an antibody which specifically binds to the antigen, which method comprises:

reacting a standard sample containing a known concentration of the analyte with the immunoreagent in a reaction vessel, to cause immunological binding between the analyte and the immunoreagent, and to form a standard sample reaction mixture, measuring the immunological binding between the analyte and the immunoreagent in the standard sample reaction mixture, reacting the test specimen suspected of containing an unknown amount of the analyte with the standard sample reaction mixture contained in the reaction vessel, to cause immunological binding between the analyte present in the test specimen and the immunoreagent, and to form a test specimen reaction mixture, measuring the immunological binding between the analyte and the immunoreagent in the test specimen reaction mixture, and determining the concentration of the analyte in the test specimen based upon the immunological binding measured in the standard sample reaction mixture and the immunological binding measured in the test specimen reaction mixture.

2. The method according to claim 1, wherein the immunological binding is measured over a time period to determine a reaction rate.

3. The method according to claim 2, wherein the concentration of analyte in the test specimen is determined based upon a ratio or difference between a reaction rate of the standard sample reaction mixture and a reaction rate of the test specimen reaction mixture.

4. The method according to claim 1, wherein the immunological binding is measured by measuring agglutination between the analyte and the immunoreagent.

5. The method according to claim 4, wherein the agglutination is measured by measuring turbidity of the standard sample and test specimen reaction mixtures.

6. The method according to claim 1, further comprising steps of preparing a calibration curve, obtained by measuring the immunological binding between a plurality of standard samples containing different known amounts of analyte and the immunoreagent, and determining the concentration of analyte in the test specimen, based upon the calibration curve.

7. The method according to claim 1, wherein two or more immunoreagents are used, and wherein at least one of the immunoreagents is labeled with a fluorescent dye or fluorescent particle.

8. The method according to claim 1, wherein the immunoreagent is immobilized on a solid phase carrier.

9. The method according to claim 1, wherein the immunological binding is measured based upon a change in the maximum resonance angle or maximum resonance adsorption wavelength of surface plasmon resonance, a change in fluorescent intensity excited by evanescent wave, a change in the frequency of quartz oscillator, a change in potential or current of an electrode, or a change in current of an ion channel.

10. The method according to claim 1, wherein the test specimen is whole blood, serum, plasma, urine, saliva, spinal fluid, fecal matter or puncture fluid.

11. The method according to claim 1, wherein the analyte is an antigen and the immunoreagent is an antibody.

12. The method according to claim 1, wherein the analyte is an antibody and the immunoreagent is an antigen.

13. The method according to claim 1, wherein the analyte is a plasma protein, a tumor-related antigen, an infectious disease-related antigen or antibody, a blood coagulation fibrinolysis-related substance, a myocardial infarction-related protein, a hormone, or a drug.

14. The method according to claim 1, wherein the immunoreagent is dissolved in a solution.

15. The method according to claim 1, wherein the immunological binding is measured by passing light through the reaction mixtures and by measuring the amount of light absorbed or scattered.

16. The method according to claim 1, wherein the immunological binding of the standard sample reaction mixture is measured for a time period of from 1 second to 10 minutes, and the immunological binding of the test specimen reaction mixture is measured for a time period of from 10 seconds to 1 hour.

17. An immunoassay method for measuring the concentration of an analyte in a test specimen, using an immunoreagent, wherein one of the analyte or the immunoreagent is an antigen, and the other of the analyte or the immunoreagent is an antibody which specifically binds to the antigen, which method comprises:

reacting the test specimen suspected of containing an unknown concentration of the analyte with the immunoreagent in a reaction vessel, to cause immunological binding between the analyte and the immunoreagent, and to form a test specimen reaction mixture, measuring the immunological binding between the analyte and the immunoreagent in the test specimen reaction mixture, reacting a standard sample containing a known amount of the analyte with the test specimen reaction mixture contained in the reaction vessel, to cause immunological binding between the analyte present in the standard sample and the immunoreagent, and to form a standard sample reaction mixture, measuring the immunological binding between the analyte and the immunoreagent in the standard sample reaction mixture, and determining the concentration of the analyte in the test specimen based upon the immunological binding measured in the standard sample reaction mixture and the immunological binding measured in test specimen reaction mixture.

* * * * *